(12) United States Patent
Udagawa

(10) Patent No.: US 11,434,475 B2
(45) Date of Patent: Sep. 6, 2022

(54) MODIFIED FILAMENTOUS FUNGAL HOST CELL FOR ENCODING A SECRETED POLYPETIDE OF INTEREST

(71) Applicant: Novozymes A/S, Bagsvaerd (DK)

(72) Inventor: Hiroaki Udagawa, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/284,163

(22) PCT Filed: Oct. 8, 2019

(86) PCT No.: PCT/EP2019/077205
§ 371 (c)(1),
(2) Date: Apr. 9, 2021

(87) PCT Pub. No.: WO2020/074502
PCT Pub. Date: Apr. 16, 2020

(65) Prior Publication Data
US 2021/0340511 A1    Nov. 4, 2021

(30) Foreign Application Priority Data
Oct. 9, 2018 (EP) .................................. 18199385

(51) Int. Cl.
*C12N 9/20* (2006.01)
*C12N 1/14* (2006.01)
*C07K 14/38* (2006.01)
*C12N 9/34* (2006.01)

(52) U.S. Cl.
CPC ............... *C12N 9/20* (2013.01); *C07K 14/38* (2013.01); *C12N 1/145* (2021.05); *C12N 9/2428* (2013.01); *C12Y 301/01003* (2013.01); *C12Y 302/01003* (2013.01)

(58) Field of Classification Search
None
See application file for complete search history.

(56) References Cited

FOREIGN PATENT DOCUMENTS

WO    2018172155 A1    9/2018

OTHER PUBLICATIONS

Chica et al. Curr Opin Biotechnol. Aug. 2005;16(4):378-84 (Year: 2005).*
Singh et al. Curr Protein Pept Sci. 2017, 18, 1-11 (Year: 2017).*
Odoni et al., 2018, Biorxiv, 1-36.
Marti-Renom, Marc A. et al., Annu. Rev. Biophys. Biomol. Struct. 2000, 29: 291-325.

* cited by examiner

*Primary Examiner* — Christian L Fronda
(74) *Attorney, Agent, or Firm* — Eric Fechter

(57) ABSTRACT

The present invention relates to filamentous fungal cells secreting a polypeptide of interest, wherein the expression of a citT gene is altered, reduced or eliminated compared to a non-mutated otherwise isogenic or parent cell, and methods of producing a secreted polypeptide of interest in said cells as well as methods of producing said cells.

29 Claims, No Drawings
Specification includes a Sequence Listing.

MODIFIED FILAMENTOUS FUNGAL HOST CELL FOR ENCODING A SECRETED POLYPETIDE OF INTEREST

CROSS-REFERENCE TO RELATED APPLICATIONS

This application is a 35 U.S.C. 371 national application of PCT/EP2019/077205, filed Oct. 8, 2019, which claims priority or the benefit from European Patent Application No. 18199385.8, filed Oct. 9, 2018. The contents of these applications are fully incorporated herein by reference.

REFERENCE TO A SEQUENCE LISTING

This application contains a Sequence Listing that was submitted as an ASCII text file named 14894-WO-PCT seq.list 8 Oct. 2019.txt (created on Oct. 8, 2019, containing 22 kb), which is incorporated herein by reference.

FIELD OF THE INVENTION

The present invention relates to modified filamentous fungal cells and to methods for producing such cells as well as methods of producing secreted polypeptides of interest therein.

BACKGROUND OF THE INVENTION

It has been shown that the citT gene in *Aspergillus niger* encodes a citrate transporter, CitT. Inactivation by split-marker gene replacement of the endogenous *A. niger* citT gene abolished the ability of this fungus to secrete citrate and, under conditions that usually favour *A. niger* citrate production, increased accumulation of extracellular oxalate (Odoni D. I. et al. *Aspergillus niger* citrate exporter revealed by comparison of two alternative citrate producing conditions, published online 23 Apr. 2018; https://doi.org/10.1101/259051).

SUMMARY OF THE INVENTION

The present invention is directed to genetically modified filamentous fungal host cells that secrete a heterologous polypeptide of interest, wherein the expression of the citT-encoded citrate transporter is altered, preferably reduced, even more preferably eliminated.

Inactivation of the citT gene may be done by any suitable gene inactivation method known in the art. An example of a convenient way to eliminate or reduce citT expression is based on techniques of gene replacement or gene interruption as it was done in Odoni D. I. et al (vide supra).

The inactivation of citT in an *Aspergillus* filamentous fungal host cell surprisingly resulted in an increased yield of a heterologous secreted polypeptide of interest expressed in the cell.

Accordingly, in a first aspect, the invention relates to mutated filamentous fungal host cells comprising a heterologous polynucleotide encoding a secreted polypeptide of interest, wherein the expression of a citT gene is altered, reduced or eliminated compared to a non-mutated otherwise isogenic or parent cell, wherein said citT gene encodes a citrate transporter polypeptide, CitT, having at least 80% amino acid sequence identity with the polypeptide of SEQ ID NO:3.

In a second aspect, the invention relates to methods of producing a secreted polypeptide of interest, said method comprising the steps of:
a) cultivating a mutated filamentous fungal host cell comprising a heterologous polynucleotide encoding the secreted polypeptide of interest under conditions conducive to the expression of the secreted polypeptide of interest, wherein the expression of a citT gene is altered, reduced or eliminated compared to a non-mutated otherwise isogenic or parent cell, and wherein said citT gene encodes a citrate transporter polypeptide, CitT, having at least 80% amino acid sequence identity with SEQ ID NO:3; and, optionally,
b) recovering the secreted polypeptide of interest.

In a final aspect, the invention relates to methods of producing a mutated filamentous fungal host cell having an improved yield and/or productivity of a secreted heterologous polypeptide of interest, said method comprising the following steps in no particular order:
a) transforming a filamentous fungal host cell with a heterologous polynucleotide encoding the secreted polypeptide of interest; and
b) mutating the host cell by altering, reducing or eliminating the expression of a citT gene in the filamentous fungal host cell, wherein said citT gene encodes a citrate transporter polypeptide, CitT, having at least 80% amino acid sequence identity with the amino acid sequence shown in SEQ ID NO:3.

Definitions cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$\text{(Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$\text{(Identical Deoxyribonucleotides} \times 100)/(\text{Length of Alignment} - \text{Total Number of Gaps in Alignment})$$

DETAILED DESCRIPTION OF THE INVENTION

Host Cells

The present invention relates to recombinant host cells comprising a polynucleotide of the present invention operably linked to one or more control sequences that direct the production and secretion of a heterologous polypeptide of interest.

A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell of the invention is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be an *Acremonium, Aspergillus, Aureobasidium, Bjerkandera, Ceriporiopsis, Chtysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma* cell.

For example, the filamentous fungal host cell may be an *Aspergillus* cell; preferably an *Aspergillus aculeatus, Aspergillus aculetinus, Aspergillus awamori, Aspergillus brasil-*

*iensis, Aspergillus foetidus, Aspergillus fumigatus, Aspergillus japonicus, Aspergillus luchuensis, Aspergillus nidulans, Aspergillus niger* or *Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chtysosporium inops, Chtysosporium keratinophilum, Chtysosporium lucknowense, Chtysosporium merdarium, Chrysosporium pannicola, Chtysosporium queenslandicum, Chtysosporium tropicum, Chtysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

In one aspect, the invention relates to methods of producing a mutated filamentous fungal host cell having an improved yield and/or productivity of a secreted heterologous polypeptide of interest, said method comprising the following steps in no particular order:
 a) transforming a filamentous fungal host cell with a heterologous polynucleotide encoding the secreted polypeptide of interest; and
 mutating the host cell by altering, reducing or eliminating the expression of a citT gene in the filamentous fungal host cell, wherein said citT gene encodes a citrate transporter polypeptide, CitT, having at least 80% amino acid sequence identity with the amino acid sequence shown in SEQ ID NO:3.

In a preferred embodiment of the aspects of the invention, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus aculeatus, Aspergillus aculetinus, Aspergillus awamori, Aspergillus brasiliensis, Aspergillus foetidus, Aspergillus fumigatus, Aspergillus japonicus, Aspergillus luchuensis, Aspergillus nidulans, Aspergillus niger* or *Aspergillus oryzae* cell.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase.

In a preferred embodiment of the invention, the citrate transporter polypeptide, CitT, comprises or consists of an amino acid sequence at least 80% identical to the amino acid sequence shown in SEQ ID NO:3; preferably at least 85%, 90%, 95%, 96%, 97%, 98% or most preferably at least 99% identical to the amino acid sequence shown in SEQ ID NO:3.

Preferably, the citT gene or homologue thereof comprises or consists of a genomic nucleotide sequence at least 80% identical to the genomic DNA sequence shown in SEQ ID NO:1; preferably at least 85%, 90%, 95%, 96%, 97%, 98% or most preferably at least 99% identical to the genomic DNA sequence shown in SEQ ID NO:1. Alternatively, the citT gene or homologue thereof comprises or consists of a genomic nucleotide sequence, the cDNA sequence of which is at least 80% identical to the cDNA sequence shown in SEQ ID NO:2; preferably at least 85%, 90%, 95%, 96%, 97%, 98% or most preferably at least 99% identical to the cDNA sequence shown in SEQ ID NO:2.

In a preferred embodiment of the invention, the yield and/or productivity of the secreted polypeptide of interest is improved in the mutated host cell of the first and second aspect compared with the non-mutated otherwise isogenic or parent cell; preferably the yield and/or productivity is improved by at least 10%, more preferably by at least 15%, 20%, 25%, 30%, 35%, 40%, 45% or by at least 50% compared with the non-mutated otherwise isogenic or parent cell.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase,

*Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Removal or Reduction of CitT Activity

The present invention also relates to methods of producing a mutant of a parent cell, which comprises inactivating, disrupting or deleting a polynucleotide, or a portion thereof, encoding a citrate transporter polypeptide, CitT, of the present invention, which results in the mutant cell producing less of the citrate transporter polypeptide, CitT, than the parent cell when cultivated under the same conditions.

The mutant cell may be constructed by reducing or eliminating expression of the citT polynucleotide or a homologue thereof using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the citT polynucleotide or homologue thereof may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

Methods for deleting or disrupting a targeted gene are described, for example, by Miller, et al (1985. Mol. Cell. Biol. 5:1714-1721); WO 90/00192; May, G. (1992. Applied Molecular Genetics of Filamentous Fungi. J. R. Kinghorn and G. Turner, eds., Blackie Academic and Professional, pp. 1-25); and Turner, G. (1994. Vectors for Genetic Manipulation. S. D. Martinelli and J. R. Kinghorn, eds., Elsevier, pp. 641-665).

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having CitT activity in a cell, comprising administering to the cell or expressing in the cell a double-stranded RNA (dsRNA) molecule, wherein the dsRNA comprises a subsequence of an citT polynucleotide or homologue thereof. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi); see, for example, U.S. Pat. No. 5,190,931.

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824 and 6,515,109.

The CitT polypeptide-deficient mutant cells are particularly useful as host cells for expression of heterologous secreted polypeptides.

The methods used for cultivation and purification of the product of interest may be performed by methods known in the art.

Methods of Production

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

One aspect of the invention relates to methods of producing a secreted polypeptide of interest, said method comprising the steps of:
 a) cultivating a filamentous fungal host cell comprising a heterologous polynucleotide encoding the secreted polypeptide of interest under conditions conducive to the expression of the secreted polypeptide of interest, wherein the expression of a citT gene is altered, reduced or eliminated compared to a non-mutated otherwise isogenic or parent cell, and wherein said citT gene encodes a citrate transporter polypeptide, CitT, having at least 80% amino acid sequence identity with SEQ ID NO:3; and, optionally,
 b) recovering the secreted polypeptide of interest.

In a preferred embodiment, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus aculeatus, Aspergillus aculetinus, Aspergillus awamori, Aspergillus brasiliensis, Aspergillus foetidus, Aspergillus fumigatus, Aspergillus japonicus, Aspergillus luchuensis, Aspergillus nidulans, Aspergillus niger* or *Aspergillus oryzae*.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

In a preferred embodiment of the invention, the citrate transporter polypeptide, CitT, comprises or consists of an amino acid sequence at least 80% identical to the amino acid sequence shown in SEQ ID NO:3; preferably at least 85%, 90%, 95%, 96%, 97%, 98% or most preferably at least 99% identical to the amino acid sequence shown in SEQ ID NO:3.

Preferably, the citT gene or homologue thereof comprises or consists of a genomic nucleotide sequence at least 80% identical to the genomic DNA sequence shown in SEQ ID NO:1; preferably at least 85%, 90%, 95%, 96%, 97%, 98% or most preferably at least 99% identical to the genomic DNA sequence shown in SEQ ID NO:1. Alternatively, the citT gene or homologue thereof comprises or consists of a genomic nucleotide sequence, the cDNA sequence of which is at least 80% identical to the cDNA sequence shown in SEQ ID NO:2; preferably at least 85%, 90%, 95%, 96%, 97%, 98% or most preferably at least 99% identical to the cDNA sequence shown in SEQ ID NO:2.

EXAMPLES

Materials and Methods

Unless otherwise stated, DNA manipulations and transformations were performed using standard methods of molecular biology as described in Sambrook et al. (1989) Molecular cloning: A laboratory manual, Cold Spring Harbor lab, Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.

Media and Solutions

AMG trace metals solution was composed of 0.3 g of citric acid, 0.68 g of $ZnCl_2$, 0.25 g of $CuSO_4.5H_2O$, 0.024 g of $NiCl_2.6H_2O$, 1.39 g of $FeSO_4.7H_2O$, 1.356 g of $MnSO_4.5H_2O$, and deionized water to 1 liter.

COVE-N-glyX plates were composed of 218 g of xylitol, 10 g of glycerol, 2.02 g of $KNO_3$, 50 ml of COVE salt solution, 25 g of Noble agar, and deionized water to 1 liter.

COVE-N plates were composed of 342.3 g of sucrose, 20 ml of COVE salt solution, 3 g of $NaNO_3$ 30 g of Noble agar, and deionized water to 1 liter.

COVE-N top agarose was composed of 342.3 g of sucrose, 20 ml of COVE salt solution, 3 g of $NaNO_3$, 10 g of low melt agarose, and deionized water to 1 liter.

COVE-N JP plates were composed of 30 g of sucrose, 20 ml of COVE salt solution, 3 g of $NaNO_3$, 30 g of Noble agar, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals was composed of 0.04 g of $Na_2B_4O_7.10H_2O$, 0.4 g of $CuSO_4.5H_2O$, 1.2 g of $FeSO_4.7H_2O$, 1.0 g of $MnSO_4.5H_2O$, 0.8 g of $Na_2MoO_4.2H_2O$, 10 g of $ZnSO_4.7H_2O$, and deionized water to 1 liter.

LB medium was composed of 10 g of tryptone, 5 g of yeast extract, 5 g of sodium chloride, and deionized water to 1 liter.

LB plus ampicillin plates were composed of 10 g of tryptone, 5 g of yeast extract, 5 g of sodium chloride, 15 g of Bacto agar, ampicillin at 100 μg per ml, and deionized water to 1 liter.

MSS medium was composed of 70 g of sucrose, 100 g of soy bean powder, three drops of pluronic antifoam, and deionized water to 1 liter; pH adjusted to 6.0.

MU-1 glu medium without urea was composed of 260 g of glucose, 3 g of $MgSO_4.7H_2O$, 6 g of $K_2SO_4$, 5 g of $KH_2PO_4$, 0.5 ml of AMG trace metals solution, a few drops of antifoam, and deionized water to 1 liter; pH adjusted to 4.5.

50% Urea was composed of 500 g of urea and deionized water to 1 liter.

YPG medium was composed of 10 g of yeast extract, 20 g of Bacto peptone, 20 g of glucose, and deionized water to 1 liter.

STC was composed of 0.8 M sorbitol, 25 mM or 50 mM Tris pH 8, and 25 mM or 50 mM $CaCl_2$).

SPTC was composed of 40% polyethyleneglycol 4000 (PEG4000) in STC buffer.

SOC medium was composed of 20 g of tryptone, 5 g of yeast extract, 0.5 g of NaCl, 10 ml of 250 mM KCl, and deionized water to 1 liter.

TAE buffer was composed of 4.84 g of Tris Base, 1.14 ml of Glacial acetic acid, 2 ml of 0.5 M EDTA pH 8.0, and deionized water to 1 liter.

Purchased Materials (*E. coli*, Plasmid and Kits)

Polymerase Chain Reaction (PCR) was carried out with the Expand™ PCR system (Boehringer Mannheim). QIAquick™ Gel Extraction Kit (Qiagen) was used for the purification of PCR fragments and extraction of DNA fragment from agarose gel. The recovered PCR fragment was incorporated into the plasmid vector with In-Fusion® HD Cloning Kit (TAKARA). *E. coli* DH5-alpha (Toyobo) was used for plasmid construction and amplification. The commercial plasmid pBluescript II SK- (Stratagene #212206) was used for cloning of PCR fragments. Amplified plasmids were recovered with Qiagen™ Plasmid Kit (Qiagen).

Strains

The expression host strain *Aspergillus niger* strains GP3-13 and C5255-2161-10 were isolated by Novozymes and are derivatives of *Aspergillus niger* NN049184 which was isolated from soil. The strain GP3-13 was genetically modified to disrupt expression of amyloglycosidase activities and alpha-amylase activities followed by the introduction of the *Gloeophyllum sepiarium* amyloglycosidase gene. The strain C5255-2161-10 was genetically modified to disrupt expression of amyloglycosidase activities and alpha-amylase activities followed by the introduction of the *Thermomyces lanuginosus* lipase gene.

Plasmids

The plasmid pHUda801 was described in example 4 in WO2012160093.

Transformation of *Aspergillus niger*

Transformation of the parent *Aspergillus niger* host cell was achieved using the general methods known for transformation in filamentous fungi, as described in the Yelton et al., "Transformation of *Aspergillus nidulans* by using a trpC plasmid," Proc Natl Acad Sci USA. 1984 March; 81(5):1470-4, and as follows:

The *Aspergillus niger* host strain was inoculated to 100 ml of YPG medium supplemented with 10 mM uridine in case the host strain is a pyrG deficient mutant, and incubated for 16 hrs at 32° C. at 80 rpm. Pellets were collected and washed with 0.6 M KCl, and resuspended 20 ml 0.6 M KCl containing a commercial beta-glucanase product (GLUCANEX™, Novozymes A/S, Bagsværd, Denmark) at a final concentration of 20 mg per ml. The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. COVE-N top agarose, the mixture was poured onto the minimum medium and the plates were incubated at 30° C. for 5 days.

PCR Amplification

| | |
|---|---|
| 5x PCR buffer (incl. MgCl2) | 20 μl |
| 2.5 mM dNTP mix | 10 μl |
| Forward primer (100 μM) | 1 μl |
| Reverse primer (100 μM) | 1 μl |
| Expand High Fidelity polymerase (Roche) | 1 μl |
| Template DNA (50-100 ng/μl) | 1 μl |
| Distilled water to | 100 μl |

| PCR conditions | | |
|---|---|---|
| 94 C. | 2 min | 1 cycle |
| 92 C. | 1 min | |
| 55 C. | 1 min | 30 cycles |
| 72 C. | 1-2 min | |
| 72 C. | 7 min | 1 cycle |

Shake Flask Cultivation for Reporter Enzyme Production

Spores of the selected transformants were inoculated in 100 ml of MSS media and cultivated at 30 C for 3 days. 10% of seed culture was transferred to MU-1 glu medium in lab-scale tanks with feeding the appropriate amounts of glucose and ammonium and cultivated at 30 C for 6 days. The supernatant was obtained by centrifugation. Culture supernatant after centrifugation was used for enzyme assay.

Glucoamylase Activity

Glucoamylase activity was measured in AmyloGlucosidase Units (AGU). AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes. An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Lipase Activity

Lipase activity was measured in KLU, Kilo Lipase Unit. Lipase enzyme was incubated (pH 8.0, 30° C.) with the substrate pNP-Palmitate (C:16). The Lipase hydrolyzes the ether bond and releases pNP which is yellow and can be detected at 405 nm. The development of colour is monitored over time (detection is kinetic) and relative to a standard.

Citrate Assay

Citrate concentration in the culture supernatants was measured in citric acid assay kit (Roche). The citrate was converted to the following three enzyme reactions.

(1) Citrate→oxaloacetate+acetate (citrate lyase)

(2) Oxaloacetate+NADH+H+→L-malate+NAD+(L-malate dehydrogenase)

(3) Pyruvate+NADH+H+→D-lactate+NAD+(D-lactate dehydrogenase)

The amount of NADH oxidized in reactions (2) and (3) is stoichiometric to the amount of citrate. NADH is determined by means of its light absence at 334, 340 and 365 nm.

Southern Hybridization

Mycelia of the selected transformants were harvested from overnight culture in 3 ml YPG medium, rinsed with distilled water. Ground mycelia were subject to genome DNA preparation using FastDNA SPIN Kit for Soil (MP Biomedicals) follows by manufacture's instruction. Non-radioactive probes were synthesized using a PCR DIG probe synthesis kit (Roche Applied Science, Indianapolis Ind.) followed by manufacture's instruction. DIG labeled probes were gel purified using a QIAquick™ Gel Extraction Kit (QIAGEN Inc., Valencia, Calif.) according to the manufacturer's instructions.

Five micrograms of genome DNA was digested with appropriate restriction enzymes completely for 16 hours (40 μl total volume, 4 U enzyme/μl DNA) and run on a 0.8% agarose gel. The DNA was fragmented in the gel by treating with 0.2 M HCl, denatured (0.5M NaOH, 1.5M NaCl) and neutralized (1M Tris, pH7.5; 1.5M NaCl) for subsequent transfer in 20×SSC to Hybond N+ membrane (Amersham). The DNA was UV cross-linked to the membrane and pre-hybridized for 1 hour at 42° C. in 20 ml DIG Easy Hyb (Roche Diagnostics Corporation, Mannheim, Germany). The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker.

Example 1: Construction of Plasmid pHUda2298, a Vector for Targeted Gene Disruption of *Aspergillus niger* citT Gene Plasmid pHUda2298 was constructed to contain 5' and 3' flanking regions for the *Aspergillus niger* citrate transporter (citT) gene separated by the *A. nidulans* orotidine-5'-phosphate decarboxylase gene (pyrG) as a selectable marker with its terminator repeats, and the human Herpes simplex virus 1 (HSV-1) thymidine kinase gene. The HSV-1 thymidine kinase gene lies 3' of the 3' flanking region of the citT gene, allowing for counter-selection of *Aspergillus niger* transformants that do not correctly target to the citT gene locus. The plasmid was constructed in several steps as described below.

A PCR product containing the 5' flanking region of *A. niger* citT was generated using the following primers:

```
Primer citT1 (sense; SEQ ID NO: 4):
5' GCTCCACCGCGGTGGCGGCCGCCGGCGTAGATCATCGCCT Primer citT2 (antisense; SEQ ID NO: 5):
5' CATTATACGAAGTTATACTAGTCAACTTAGCATACAGATT
```

The desired fragment was amplified by PCR in a reaction composed of approximately 100 ng of genome DNA of *Aspergillus niger* NN049184, 1 μl of Expand High Fidelity polymerase (Roche), 100 μM of primer citT1, 100 μM of primer citT2, 5×PCR buffer (incl.MgCl2), 20 μl 2.5 mM dNTP mix (total volume; 100 μl). The reaction was incubated in a Bio-Rad® C1000 Touch™ Thermal Cycler programmed for 1 cycle at 94° C. for 2 minutes; 30 cycles each at 94° C. for 30 seconds, 55° C. for 30 seconds, and 72° C. for 2 minutes; 1 cycle at 72° C. for 7 minutes; and a 4° C. hold. The resulting 2,016 bp PCR fragment was purified by 0.8% agarose gel electrophoresis using TAE buffer, excised from the gel, and extracted using a QIAQUICK® Gel Extraction Kit. The purified 2,016 bp PCR fragment was digested by NotI and SpeI.

Plasmid pHUda801 (Example 4 in WO 2012160093 A1) was digested with Not I and SpeI, and purified by 0.8% agarose gel electrophoresis using TAE buffer, where a 9,558 bp fragment was excised from the gel and extracted using a QIAQUICK® Gel Extraction Kit. The 2,016 bp fragment was incorporated into the 9,558 bp PCR fragment in a reaction composed of 1 μl of the 9,558 bp fragment, 3 μl of the 2,016 bp fragment, 3 μl of H₂O and 2 μl of In-Fusion® HD Cloning Kit (TAKARA). The infusion reaction was incubated at 50° C. for 10 minutes. Five μl of the mixture were transformed into DH5☐ chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHUda801-5'citT.

A PCR product containing the 3' flanking region of *A. niger* citT was generated using the following primers:

```
Primer citT3 (sense; SEQ ID NO: 6):
5' TGCTATACGAAGTTATGTTTAAACTCGGAAGAAAGAGGTAGC Primer citT4 (antisense; SEQ ID NO: 7):
5' GGCGAATTCGTTTGTGTTAATTAAAAACAGGGATACTCTACA
```

The desired fragment was amplified by PCR in a reaction composed of approximately 100 ng of genome DNA of *Aspergillus niger* NN049184, 1 μl of Expand High Fidelity polymerase (Roche), 100 μM of primer citT3, 100 μM of primer citT4, 5×PCR buffer (incl.MgCl2), 20 μl 2.5 mM dNTP mix (total volume; 100 μl). The reaction was incubated in a Bio-Rad® C1000 Touch™ Thermal Cycler programmed for 1 cycle at 94° C. for 2 minutes; 30 cycles each at 94° C. for 30 seconds, 55° C. for 30 seconds, and 72° C. for 2 minutes; 1 cycle at 72° C. for 7 minutes; and a 4° C. hold. The resulting 1,645 bp PCR fragment was purified by 0.8% agarose gel electrophoresis using TAE buffer, excised from the gel, and extracted using a QIAQUICK® Gel Extraction Kit. The purified 1,645 bp PCR fragment was digested by PmeI and PacI. Plasmid pHUda801-5'citT was digested with PmeI and PacI, and purified by 0.8% agarose gel electrophoresis using TAE buffer, where a 11,989 bp fragment was excised from the gel and extracted using a QIAQUICK® Gel Extraction Kit. The 1,645 bp PCR fragment was incorporated into the 11,989 bp fragment in a reaction composed of 1 μl of the 11,989 bp fragment, 3 μl of the 1,645 bp fragment, 3 μl of the 1,645 bp fragment, 3 μl of H₂O and 2 μl of In-Fusion® HD Cloning Kit (TAKARA). The infusion reaction was incubated at 50° C. for 10 minutes. Five μl of the ligation mixture were transformed into DH5☐ chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHUda2298.

Example 2: The *Aspergillus niger* citT Gene Disruption in GP3-13 and C5255-2161-10

The pyrG gene in GP3-13 and C5255-2161-10 was rescued as follows. The strains GP3-13 and C5255-2161-10 were inoculated on Cove-N JP media containing 10 mM uridine and 1 g/L 5-fluoro-orotic acid (5-FOA) at 30° C. for 5 days. Strains in which the pyrG gene has been deleted will grow in the presence of 5-FOA; those that retain the gene will convert 5-FOA to 5-fluoro-UMP, a toxic intermediate. The grown colonies were transferred with sterile toothpicks to COVE-N-gly plates supplemented with 10 mM uridine and were grown at 30° C. for 7 days. The isolated strain was named GP3-13-P1 and C5255-2161-10-P1, respectively.

Protoplasts of *Aspergillus niger* strains GP3-13-P1 and C5255-2161-10-P1, were prepared by cultivating the strain in 100 ml of YPG medium supplemented with 10 mM uridine at 32° C. for 16 hours with gentle agitation at 80 rpm. Pellets were collected and washed with 0.6 M KCl, and resuspended 20 ml 0.6 M KCl containing a commercial β-glucanase product (GLUCANEX™, Novozymes A/S, Bagsværd, Denmark) at a final concentration of 20 mg per ml. The suspension was incubated at 32° C. at 80 rpm until protoplasts were formed. Protoplasts were filtered through a funnel lined with MIRACLOTH® into a 50 ml sterile plastic centrifuge tube and were washed with 0.6 M KCl to extract trapped protoplasts. The combined filtrate and supernatant were collected by centrifugation at 2,000 rpm for 15 minutes. The supernatant was discarded and the pellet was washed with 10-25 ml of STC and centrifuged again at 2,000 rpm for 10 minutes and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml.

Approximately 10 µg of pHUda2298 was added to 0.3 ml of the protoplast suspension, mixed gently, and incubated on ice for 30 minutes. Three ml of SPTC was added and the protoplast suspension was incubated for 20 minutes at 37° C. After the addition of 12 ml of 50° C. COVE-N top agarose, the mixture was poured onto the COVE-N plates and the plates were incubated at 30° C. for 7 days. The grown transformants were transferred with sterile toothpicks to Cove-N JP plates supplemented with 1.5 µM 5-Flouro-2-deoxyuridine (FdU), an agent which kills cells expressing the herpes simplex virus (HSV) thymidine kinase gene (TK) harboring in pHUda2298. Single spore isolates were transferred to COVE-N-glyX plates.

Possible transformants of Aspergillus niger strain GP3-13-P1 and C5255-2161-10-P1 containing the pHUda2298 to disrupt citT gene were screened by Southern analysis. Each of the spore purified transformants were cultivated in 3 ml of YPG medium and incubated at 30° C. for 2 days with shaking at 200 rpm. Biomass was collected using a MIRACLOTH® lined funnel. Ground mycelia were subject to genome DNA preparation using FastDNA SPIN Kit for Soil (MP Biomedicals) follows by manufacture's instruction.

Southern blot analysis was performed to confirm the disruption of the citT gene locus. Five µg of genomic DNA from each transformant were digested with HindIII. The genomic DNA digestion reactions were composed of 5 µg of genomic DNA, 1 µl of HindIII, 2 µl of 10× cut smart buffer, and water to 20 µl. Genomic DNA digestions were incubated at 37° C. for approximately 16 hours. The digestions were submitted to 0.8% agarose gel electrophoresis using TAE buffer and blotted onto a hybond N+ (GE Healthcare Life Sciences, Manchester, N.H., USA) using a TURBOBLOTTER® for approximately 1 hour following the manufacturer's recommendations. The membrane was hybridized with a 500 bp digoxigenin-labeled Aspergillus niger citT probe, which was synthesized by incorporation of digoxigenin-11-dUTP by PCR using primers citT5 (sense) and citT6 (antisense) shown below.

```
Forward primer (citT5; SEQ ID NO: 8):
5'-GAACCCCAGAAGCTGGGAGC

Reverse primer (citT6; SEQ ID NO: 9):
5'-GGTAGACGGCCTGTCTTTAT
```

The amplification reaction (100 µl) was composed of 200 µM PCR DIG Labeling Mix (vial 2) (Roche Applied Science, Palo Alto, Calif., USA), 0.5 µM primers, EXPAND® High Fidelity Enzyme mix (vial 1) (Roche Applied Science, Palo Alto, USA), and 1 µl (100 µg/µl) of pHUda2298 as template in a final volume of 100 µl. The amplification reaction was incubated in a Bio-Rad® C1000 Touch™ Thermal Cycler programmed for 1 cycle at 94° C. for 2 minutes; 30 cycles each at 94° C. for 30 seconds, 55° C. for 30 seconds, and 72° C. for 30 seconds and a 4° C. hold. PCR products were separated by 0.8% agarose gel electrophoresis using TAE buffer where a 0.5 kb fragment was excised from the gel and extracted using a QIAQUICK® Gel Extraction Kit. The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker. Strains, GP3-2298-1, 2, 3 and C5255-2161-2298-2, 4, 7, giving the correct integration at the citT loci (a hybridized band shifted from 5.1 kb to 4.0 kb) generated from GP3-13-P1 and C5255-2161-10-P1, respectively, were selected for the subsequent experiments.

Example 3: Shake Flask Fermentations of the citT Gene Disruptants

Aspergillus niger strains GP3-2298-1, 2, 3, C5255-2161-2298-2, 4, 7 and their parent strains GP3-13 and C5255-2161-10 were cultivated on COVE-N-glyX plates at 30° C. for about a week. A sterile transfer pipette was used to punch a piece of small plugs from each plate, which were each inoculated into 100 ml of MSS medium in 500 ml flasks. The flasks were incubated at 30° C. for 3 days at 200 rpm. And then, 10 ml of culture broth was transferred to 100 ml of MU1 glu medium in 500 ml flasks.

The flasks were incubated at 32° C. for 6 days at 200 rpm. Each culture was centrifuged at 5,000 rpm for 10 minutes in a 10 ml test tubes and culture supernatant was recovered for determining either glucoamylase (AG; see table 1) or lipase (KLU; see table 2) productivities. Also, citrate amounts were determined in the culture supernatants followed by materials and methods. Enzyme productivities were determined by extrapolation from the generated standard curve and compared to the Aspergillus niger strain GP3-13 and C5255-2161-10 set at 100%.

The citT gene disrupted strain gave 60~75% higher lipase productivity or 12~20% higher glucoamylase productivity, respectively, than a non-mutated reference Aspergillus niger strain.

TABLE 1

Glucoamylase and citrate productivities in shake flask culture.

| Sample Name | Relative glucoamylase productivity (%) | Citrate production (%) |
| --- | --- | --- |
| GP3-2298-1 | 120% | 3.3% |
| GP3-2298-2 | 115% | 3.1% |
| GP3-2298-3 | 112% | 2.8% |
| GP3-13 | 100% | 100% |

TABLE 2

Lipase and citrate productivities in shake flask culture.

| Sample Name | Relative lipase productivity (%) | Citrate production (%) |
| --- | --- | --- |
| C5255-2161-2298-2 | 163% | 2.6% |
| C5255-2161-2298-4 | 175% | 2.7% |
| C5255-2161-2298-7 | 176% | 2.5% |
| C5255-2161-10 | 100% | 100% |

The invention claimed is:

1. A mutated filamentous fungal host cell comprising a heterologous polynucleotide encoding a secreted polypeptide of interest, wherein the expression of an endogenous citT gene is reduced or eliminated compared to a non-mutated otherwise isogenic or parent cell, wherein said citT gene encodes a citrate transporter polypeptide, CitT, having at least 80% amino acid sequence identity with the polypeptide of SEQ ID NO: 3.

2. The host cell of claim 1 which is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*.

3. The host cell of claim 2 which is an *Aspergillus aculeatus, Aspergillus aculetinus, Aspergillus awamori, Aspergillus brasiliensis, Aspergillus foetidus, Aspergillus fumigatus, Aspergillus japonicus, Aspergillus luchuensis, Aspergillus nidulans, Aspergillus niger* or *Aspergillus oryzae*.

4. The host cell of claim 1, wherein the secreted polypeptide of interest is an enzyme.

5. The host cell of claim 1, wherein the citrate transporter polypeptide, CitT, comprises or consists of an amino acid sequence at least 95% identical to the amino acid sequence shown in SEQ ID NO: 3.

6. The host cell of claim 1, wherein the citT gene or homologue thereof comprises or consists of a genomic nucleotide sequence at least 80% identical to the genomic DNA sequence shown in SEQ ID NO: 1.

7. The host cell of claim 1, wherein the citT gene or homologue thereof comprises or consists of a genomic nucleotide sequence, the cDNA sequence of which is at least 80% identical to the cDNA sequence shown in SEQ ID NO: 2.

8. The host cell of claim 1, wherein the yield and/or productivity of the secreted polypeptide of interest is improved compared with the non-mutated otherwise isogenic or parent cell.

9. A method of producing a secreted polypeptide of interest, said method comprising the steps of:
   a) cultivating a mutated filamentous fungal host cell comprising a heterologous polynucleotide encoding the secreted polypeptide of interest under conditions conducive to the expression of the secreted polypeptide of interest, wherein the expression of an endogenous citT gene is reduced or eliminated compared to a non-mutated otherwise isogenic or parent cell, and wherein said citT gene encodes a citrate transporter polypeptide, CitT, having at least 80% amino acid sequence identity with SEQ ID NO: 3; and,
b) recovering the secreted polypeptide of interest.

10. The method of claim 9, wherein the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*.

11. The method cell of claim 10, wherein the filamentous fungal host cell is an *Aspergillus aculeatus, Aspergillus aculetinus, Aspergillus awamori, Aspergillus brasiliensis, Aspergillus foetidus, Aspergillus fumigatus, Aspergillus japonicus, Aspergillus luchuensis, Aspergillus nidulans, Aspergillus niger* or *Aspergillus oryzae*.

12. The method of claim 9, wherein the secreted polypeptide of interest is an enzyme.

13. The method of claim 9, wherein the citrate transporter polypeptide, CitT, comprises or consists of an amino acid sequence at least 95% identical to the amino acid sequence shown in SEQ ID NO: 3.

14. The method of claim 9, wherein the citT gene or homologue thereof comprises or consists of a genomic nucleotide sequence at least 80% identical to the genomic DNA sequence shown in SEQ ID NO: 1.

15. The method of claim 9, wherein the citT gene or homologue thereof comprises or consists of a genomic nucleotide sequence, the cDNA sequence of which is at least 80% identical to the cDNA sequence shown in SEQ ID NO: 2.

16. The method of claim 9, wherein the yield and/or productivity of the secreted polypeptide of interest is improved compared with the non-mutated otherwise isogenic or parent cell.

17. A method of producing a mutated filamentous fungal host cell having an improved yield and/or productivity of a secreted heterologous polypeptide of interest, said method comprising the following steps in no particular order:
a) transforming a filamentous fungal host cell with a heterologous polynucleotide encoding the secreted polypeptide of interest; and
b) mutating the host cell by reducing or eliminating the expression of an endogenous citT gene in the filamentous fungal host cell, wherein said citT gene encodes a citrate transporter polypeptide, CitT, having at least 80% amino acid sequence identity with the amino acid sequence shown in SEQ ID NO: 3.

18. The method of claim 17, wherein the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*.

19. The method of claim 18, wherein the filamentous fungal host cell is an *Aspergillus aculeatus, Aspergillus aculetinus, Aspergillus awamori, Aspergillus brasiliensis, Aspergillus foetidus, Aspergillus fumigatus, Aspergillus japonicus, Aspergillus luchuensis, Aspergillus nidulans, Aspergillus niger* or *Aspergillus oryzae*.

20. The method of claim 17, wherein the secreted polypeptide of interest is an enzyme.

21. The method of claim 17, wherein the citrate transporter polypeptide, CitT, comprises or consists of an amino acid sequence at least 95% identical to the amino acid sequence shown in SEQ ID NO: 3.

22. The method of claim 17, wherein the citT gene or homologue thereof comprises or consists of a genomic nucleotide sequence at least 80% identical to the genomic DNA sequence shown in SEQ ID NO: 1.

23. The method of claim 17, wherein the citT gene or homologue thereof comprises or consists of a genomic nucleotide sequence, the cDNA sequence of which is at least 80% identical to the cDNA sequence shown in SEQ ID NO: 2.

24. The host cell of claim 1, wherein the citrate transporter polypeptide, CitT, comprises or consists of an amino acid sequence at least 90% identical to the amino acid sequence shown in SEQ ID NO: 3.

25. The host cell of claim 1, wherein the citrate transporter polypeptide, CitT, comprises or consists of an amino acid sequence at least 98% identical to the amino acid sequence shown in SEQ ID NO: 3.

26. The method of claim 9, wherein the citrate transporter polypeptide, CitT, comprises or consists of an amino acid sequence at least 90% identical to the amino acid sequence shown in SEQ ID NO: 3.

27. The method of claim 9, wherein the citrate transporter polypeptide, CitT, comprises or consists of an amino acid sequence at least 98% identical to the amino acid sequence shown in SEQ ID NO: 3.

28. The method of claim 17, wherein the citrate transporter polypeptide, CitT, comprises or consists of an amino acid sequence at least 90% identical to the amino acid sequence shown in SEQ ID NO: 3.

29. The method of claim 17, wherein the citrate transporter polypeptide, CitT, comprises or consists of an amino acid sequence at least 98% identical to the amino acid sequence shown in SEQ ID NO: 3.

* * * * *

SEQUENCE LISTING

<160> NUMBER OF SEQ ID NOS: 9

<210> SEQ ID NO 1
<211> LENGTH: 1790
<212> TYPE: DNA
<213> ORGANISM: Aspergillus niger
<220> FEATURE:
<221> NAME/KEY: exon
<222> LOCATION: (1)..(261)
<223> OTHER INFORMATION: Genomic citT sequence
<220> FEATURE:
<221> NAME/KEY: Intron
<222> LOCATION: (262)..(318)
<223> OTHER INFORMATION: Genomic citT sequence
<220> FEATURE:
<221> NAME/KEY: exon
<222> LOCATION: (319)..(559)
<220> FEATURE:
<221> NAME/KEY: Intron
<222> LOCATION: (560)..(608)
<223> OTHER INFORMATION: Genomic citT sequence
<220> FEATURE:
<221> NAME/KEY: exon
<222> LOCATION: (609)..(677)
<223> OTHER INFORMATION: Genomic citT sequence
<220> FEATURE:
<221> NAME/KEY: Intron
<222> LOCATION: (678)..(727)
<223> OTHER INFORMATION: Genomic citT sequence
<220> FEATURE:
<221> NAME/KEY: exon
<222> LOCATION: (728)..(1174)
<223> OTHER INFORMATION: Genomic citT sequence
<220> FEATURE:
<221> NAME/KEY: Intron
<222> LOCATION: (1175)..(1233)
<223> OTHER INFORMATION: Genomic citT sequence
<220> FEATURE:
<221> NAME/KEY: exon
<222> LOCATION: (1234)..(1787)
<223> OTHER INFORMATION: Genomic citT sequence

<400> SEQUENCE: 1

```
atg tct tca acc acg tct tca tca aga tca gac ctt gaa aag gtc ccc      48
Met Ser Ser Thr Thr Ser Ser Ser Arg Ser Asp Leu Glu Lys Val Pro
1               5                   10                  15 gta cca cag gtc atc cct aga gac agt gac tcc gat aag gga tcc ctc      96
Val Pro Gln Val Ile Pro Arg Asp Ser Asp Ser Asp Lys Gly Ser Leu
            20                  25                  30 tct ccg gag cct tcg acc cta gag gct cag tca tcc gag aag cca ccg     144
Ser Pro Glu Pro Ser Thr Leu Glu Ala Gln Ser Ser Glu Lys Pro Pro
        35                  40                  45 cat cat atc ttc aca cgg tct cgc aag ctg caa atg gtt tgc atc gtc     192
His His Ile Phe Thr Arg Ser Arg Lys Leu Gln Met Val Cys Ile Val
    50                  55                  60 tcc ctc gct gcc ata ttt tct ccg ctt tcg tcg aac att tac ttc cct     240
Ser Leu Ala Ala Ile Phe Ser Pro Leu Ser Ser Asn Ile Tyr Phe Pro
65                  70                  75                  80 gcc ctg gat gat gtc tcg aaa gtaagtactt cggctccatg ccatcctgga        291
Ala Leu Asp Asp Val Ser Lys
                85 cctgacatgt tgacggtacc atgatag tcc ctc aac atc agc atg tcg ctc gca   345
                                Ser Leu Asn Ile Ser Met Ser Leu Ala
                                                90                  95 aca ctc acc atc acg gtg tac atg atc gtc caa ggc ctc gct ccc agc     393
Thr Leu Thr Ile Thr Val Tyr Met Ile Val Gln Gly Leu Ala Pro Ser
                100                 105                 110 ttc tgg ggt tcc atg tca gac gcc aca ggt aga cgg cct gtc ttt att     441
Phe Trp Gly Ser Met Ser Asp Ala Thr Gly Arg Arg Pro Val Phe Ile
```

|  |  |
|---|---:|
| ```
            115                 120                 125
gga aca ttc att gtt tac ctc gta gcc aat att gct ctg gcc gaa tcc
Gly Thr Phe Ile Val Tyr Leu Val Ala Asn Ile Ala Leu Ala Glu Ser
    130                 135                 140
``` | 489 |
| ```
aag aac tat ggt gag ctc atg gcc ttc cga gcc ttg cag gct gct ggt
Lys Asn Tyr Gly Glu Leu Met Ala Phe Arg Ala Leu Gln Ala Ala Gly
145                 150                 155                 160
``` | 537 |
| ```
agc gcg gcc acc atc tca atc g gtaagagcga tctcacagcc tagcatagca
Ser Ala Ala Thr Ile Ser Ile
                165
``` | 589 |
| ```
tctcgctaac caagattag ga  gct gga gtg att ggt gat atc aca aac tcg
                        Gly Ala Gly Val Ile Gly Asp Ile Thr Asn Ser
                            170                 175
``` | 640 |
| ```
gaa gaa aga ggt agc ttg gtg ggt atc ttc ggt gga g gttagaaaac
Glu Glu Arg Gly Ser Leu Val Gly Ile Phe Gly Gly
    180                 185                 190
``` | 687 |
| ```
atcccttgc ttgctggatg gtgaagctga cagaaccaag tt  cgc atg ctt gga
                                                Val Arg Met Leu Gly
                                                              195
``` | 741 |
| ```
cag gga atc ggg ccg gtt ttc ggc ggc att ttc acc cag tat ctc gga
Gln Gly Ile Gly Pro Val Phe Gly Gly Ile Phe Thr Gln Tyr Leu Gly
                    200                 205                 210
``` | 789 |
| ```
tat cga tct atc ttt tgg ttc ctc acg att gct gga ggc gtg agt ctc
Tyr Arg Ser Ile Phe Trp Phe Leu Thr Ile Ala Gly Gly Val Ser Leu
            215                 220                 225
``` | 837 |
| ```
ctg tcc att ctg gtg ctt ctt ccg gag aca ttg aga cca att gct gga
Leu Ser Ile Leu Val Leu Leu Pro Glu Thr Leu Arg Pro Ile Ala Gly
        230                 235                 240
``` | 885 |
| ```
aat gga act gtg aag ctc aat ggc att cat aag ccc ttc atc tac acg
Asn Gly Thr Val Lys Leu Asn Gly Ile His Lys Pro Phe Ile Tyr Thr
    245                 250                 255
``` | 933 |
| ```
atc acc ggc cag acg ggg gtt gtc gag gga gcg caa ccg gaa gcg aaa
Ile Thr Gly Gln Thr Gly Val Val Glu Gly Ala Gln Pro Glu Ala Lys
260                 265                 270                 275
``` | 981 |
| ```
aag acc aaa acc agc tgg aag tct gtt ttt gct cct ttg aca ttc ctc
Lys Thr Lys Thr Ser Trp Lys Ser Val Phe Ala Pro Leu Thr Phe Leu
                280                 285                 290
``` | 1029 |
| ```
gtc gaa aag gac gtt ttc atc acc ctg ttc ttt gga agt atc gtg tac
Val Glu Lys Asp Val Phe Ile Thr Leu Phe Phe Gly Ser Ile Val Tyr
            295                 300                 305
``` | 1077 |
| ```
aca gtg tgg agc atg gtg aca tcc agt acc acc gac ctc ttc agc gaa
Thr Val Trp Ser Met Val Thr Ser Ser Thr Thr Asp Leu Phe Ser Glu
        310                 315                 320
``` | 1125 |
| ```
gtg tac ggc ctg tca tcc ctg gac att gga ctc act ttc cta ggc aat g
Val Tyr Gly Leu Ser Ser Leu Asp Ile Gly Leu Thr Phe Leu Gly Asn
    325                 330                 335
``` | 1174 |
| ```
gtaagtttta tgatctcctc cgacactttt ggcctgaatg accgctcatg cactggtag
``` | 1233 |
| ```
gc ttt gga tgt atg tct ggc tct tat ctg gtc ggc tac ctt atg gat
   Gly Phe Gly Cys Met Ser Gly Ser Tyr Leu Val Gly Tyr Leu Met Asp
   340                 345                 350                 355
``` | 1280 |
| ```
tac aac cac cgt ctt acc gaa cgc gaa tat tgc gag aaa cac ggt tat
Tyr Asn His Arg Leu Thr Glu Arg Glu Tyr Cys Glu Lys His Gly Tyr
                360                 365                 370
``` | 1328 |
| ```
ccg gca ggc aca cgt gtc aat ctg aaa tca cac ccc gac ttc ccc att
Pro Ala Gly Thr Arg Val Asn Leu Lys Ser His Pro Asp Phe Pro Ile
            375                 380                 385
``` | 1376 |
| ```
gag gtc gcc cgg atg cgc aat acc tgg tgg gtg att gcg atc ttc atc
Glu Val Ala Arg Met Arg Asn Thr Trp Trp Val Ile Ala Ile Phe Ile
        390                 395                 400
``` | 1424 |

```
gtg aca gtt gct ttg tac ggc gtg tct ttg cgg aca cat ctg gcg gtg    1472
Val Thr Val Ala Leu Tyr Gly Val Ser Leu Arg Thr His Leu Ala Val
    405                 410                 415 cct atc att ctg cag tac ttc att gcg ttc tgc tca aca gga ctc ttc    1520
Pro Ile Ile Leu Gln Tyr Phe Ile Ala Phe Cys Ser Thr Gly Leu Phe
420                 425                 430                 435 acc atc aac agc gcc ctg gtc atc gat ctt tac cca ggt gct agc gcc    1568
Thr Ile Asn Ser Ala Leu Val Ile Asp Leu Tyr Pro Gly Ala Ser Ala
                440                 445                 450 agt gcg aca gca gtg aac aat ctg atg cgg tgc ctg ctt gga gct ggc    1616
Ser Ala Thr Ala Val Asn Asn Leu Met Arg Cys Leu Leu Gly Ala Gly
            455                 460                 465 ggt gtg gct atc gtg caa cct atc ctg gac gcc ttg aag ccg gat tat    1664
Gly Val Ala Ile Val Gln Pro Ile Leu Asp Ala Leu Lys Pro Asp Tyr
        470                 475                 480 act ttc ctc ttg ctt gcc ggc atc acc ctc gtg atg act ccg ttg ctg    1712
Thr Phe Leu Leu Leu Ala Gly Ile Thr Leu Val Met Thr Pro Leu Leu
    485                 490                 495 tac gtc gaa gat cga tgg ggt cct ggc tgg cga cat gcc cgc gaa agg    1760
Tyr Val Glu Asp Arg Trp Gly Pro Gly Trp Arg His Ala Arg Glu Arg
500                 505                 510                 515 aga ctc aag gcc aaa gcc aac ggc aac tag                            1790
Arg Leu Lys Ala Lys Ala Asn Gly Asn
                520

<210> SEQ ID NO 2
<211> LENGTH: 1575
<212> TYPE: DNA
<213> ORGANISM: Artificial sequence
<220> FEATURE:
<223> OTHER INFORMATION: cDNA of SEQ ID NO:1
<220> FEATURE:
<221> NAME/KEY: CDS
<222> LOCATION: (1)..(1572)
<223> OTHER INFORMATION: cDNA encoding the citrate transporter CitT of
      SEQ ID NO:3.

<400> SEQUENCE: 2 atg tct tca acc acg tct tca tca aga tca gac ctt gaa aag gtc ccc      48
Met Ser Ser Thr Thr Ser Ser Ser Arg Ser Asp Leu Glu Lys Val Pro
1               5                   10                  15 gta cca cag gtc atc cct aga gac agt gac tcc gat aag gga tcc ctc      96
Val Pro Gln Val Ile Pro Arg Asp Ser Asp Ser Asp Lys Gly Ser Leu
            20                  25                  30 tct ccg gag cct tcg acc cta gag gct cag tca tcc gag aag cca ccg     144
Ser Pro Glu Pro Ser Thr Leu Glu Ala Gln Ser Ser Glu Lys Pro Pro
        35                  40                  45 cat cat atc ttc aca cgg tct cgc aag ctg caa atg gtt tgc atc gtc     192
His His Ile Phe Thr Arg Ser Arg Lys Leu Gln Met Val Cys Ile Val
    50                  55                  60 tcc ctc gct gcc ata ttt tct ccg ctt tcg tcg aac att tac ttc cct     240
Ser Leu Ala Ala Ile Phe Ser Pro Leu Ser Ser Asn Ile Tyr Phe Pro
65                  70                  75                  80 gcc ctg gat gat gtc tcg aaa tcc ctc aac atc agc atg tcg ctc gca     288
Ala Leu Asp Asp Val Ser Lys Ser Leu Asn Ile Ser Met Ser Leu Ala
                85                  90                  95 aca ctc acc atc acg gtg tac atg atc gtc caa ggc ctc gct ccc agc     336
Thr Leu Thr Ile Thr Val Tyr Met Ile Val Gln Gly Leu Ala Pro Ser
            100                 105                 110 ttc tgg ggt tcc atg tca gac gcc aca ggt aga cgg cct gtc ttt att     384
Phe Trp Gly Ser Met Ser Asp Ala Thr Gly Arg Arg Pro Val Phe Ile
        115                 120                 125
```

| | | |
|---|---|---|
| gga aca ttc att gtt tac ctc gta gcc aat att gct ctg gcc gaa tcc<br>Gly Thr Phe Ile Val Tyr Leu Val Ala Asn Ile Ala Leu Ala Glu Ser<br>130                  135                  140 | | 432 |
| aag aac tat ggt gag ctc atg gcc ttc cga gcc ttg cag gct gct ggt<br>Lys Asn Tyr Gly Glu Leu Met Ala Phe Arg Ala Leu Gln Ala Ala Gly<br>145                  150                155                160 | | 480 |
| agc gcg gcc acc atc tca atc gga gct gga gtg att ggt gat atc aca<br>Ser Ala Ala Thr Ile Ser Ile Gly Ala Gly Val Ile Gly Asp Ile Thr<br>                165                170                175 | | 528 |
| aac tcg gaa gaa aga ggt agc ttg gtg ggt atc ttc ggt gga gtt cgc<br>Asn Ser Glu Glu Arg Gly Ser Leu Val Gly Ile Phe Gly Gly Val Arg<br>        180                185                190 | | 576 |
| atg ctt gga cag gga atc ggg ccg gtt ttc ggc ggc att ttc acc cag<br>Met Leu Gly Gln Gly Ile Gly Pro Val Phe Gly Gly Ile Phe Thr Gln<br>     195               200                205 | | 624 |
| tat ctc gga tat cga tct atc ttt tgg ttc ctc acg att gct gga ggc<br>Tyr Leu Gly Tyr Arg Ser Ile Phe Trp Phe Leu Thr Ile Ala Gly Gly<br>210                  215                220 | | 672 |
| gtg agt ctc ctg tcc att ctg gtg ctt ctt ccg gag aca ttg aga cca<br>Val Ser Leu Leu Ser Ile Leu Val Leu Leu Pro Glu Thr Leu Arg Pro<br>225                  230                235                240 | | 720 |
| att gct gga aat gga act gtg aag ctc aat ggc att cat aag ccc ttc<br>Ile Ala Gly Asn Gly Thr Val Lys Leu Asn Gly Ile His Lys Pro Phe<br>                245                250                255 | | 768 |
| atc tac acg atc acc ggc cag acg ggg gtt gtc gag gga gcg caa ccg<br>Ile Tyr Thr Ile Thr Gly Gln Thr Gly Val Val Glu Gly Ala Gln Pro<br>        260                265                270 | | 816 |
| gaa gcg aaa aag acc aaa acc agc tgg aag tct gtt ttt gct cct ttg<br>Glu Ala Lys Lys Thr Lys Thr Ser Trp Lys Ser Val Phe Ala Pro Leu<br>     275               280                285 | | 864 |
| aca ttc ctc gtc gaa aag gac gtt ttc atc acc ctg ttc ttt gga agt<br>Thr Phe Leu Val Glu Lys Asp Val Phe Ile Thr Leu Phe Phe Gly Ser<br>290                  295                300 | | 912 |
| atc gtg tac aca gtg tgg agc atg gtg aca tcc agt acc acc gac ctc<br>Ile Val Tyr Thr Val Trp Ser Met Val Thr Ser Ser Thr Thr Asp Leu<br>305                  310                315                320 | | 960 |
| ttc agc gaa gtg tac ggc ctg tca tcc ctg gac att gga ctc act ttc<br>Phe Ser Glu Val Tyr Gly Leu Ser Ser Leu Asp Ile Gly Leu Thr Phe<br>                325                330                335 | | 1008 |
| cta ggc aat ggc ttt gga tgt atg tct ggc tct tat ctg gtc ggc tac<br>Leu Gly Asn Gly Phe Gly Cys Met Ser Gly Ser Tyr Leu Val Gly Tyr<br>        340                345                350 | | 1056 |
| ctt atg gat tac aac cac cgt ctt acc gaa cgc gaa tat tgc gag aaa<br>Leu Met Asp Tyr Asn His Arg Leu Thr Glu Arg Glu Tyr Cys Glu Lys<br>     355               360                365 | | 1104 |
| cac ggt tat ccg gca ggc aca cgt gtc aat ctg aaa tca cac ccc gac<br>His Gly Tyr Pro Ala Gly Thr Arg Val Asn Leu Lys Ser His Pro Asp<br>370                  375                380 | | 1152 |
| ttc ccc att gag gtc gcc cgg atg cgc aat acc tgg tgg gtg att gcg<br>Phe Pro Ile Glu Val Ala Arg Met Arg Asn Thr Trp Trp Val Ile Ala<br>385                  390                395                400 | | 1200 |
| atc ttc atc gtg aca gtt gct ttg tac ggc gtg tct ttg cgg aca cat<br>Ile Phe Ile Val Thr Val Ala Leu Tyr Gly Val Ser Leu Arg Thr His<br>                405                410                415 | | 1248 |
| ctg gcg gtg cct atc att ctg cag tac ttc att gcg ttc tgc tca aca<br>Leu Ala Val Pro Ile Ile Leu Gln Tyr Phe Ile Ala Phe Cys Ser Thr<br>        420                425                430 | | 1296 |
| gga ctc ttc acc atc aac agc gcc ctg gtc atc gat ctt tac cca ggt<br>Gly Leu Phe Thr Ile Asn Ser Ala Leu Val Ile Asp Leu Tyr Pro Gly | | 1344 |

```
                    435                 440                 445
gct agc gcc agt gcg aca gca gtg aac aat ctg atg cgg tgc ctg ctt      1392
Ala Ser Ala Ser Ala Thr Ala Val Asn Asn Leu Met Arg Cys Leu Leu
450                 455                 460 gga gct ggc ggt gtg gct atc gtg caa cct atc ctg gac gcc ttg aag      1440
Gly Ala Gly Gly Val Ala Ile Val Gln Pro Ile Leu Asp Ala Leu Lys
465                 470                 475                 480 ccg gat tat act ttc ctc ttg ctt gcc ggc atc acc ctc gtg atg act      1488
Pro Asp Tyr Thr Phe Leu Leu Leu Ala Gly Ile Thr Leu Val Met Thr
                485                 490                 495 ccg ttg ctg tac gtc gaa gat cga tgg ggt cct ggc tgg cga cat gcc      1536
Pro Leu Leu Tyr Val Glu Asp Arg Trp Gly Pro Gly Trp Arg His Ala
                500                 505                 510 cgc gaa agg aga ctc aag gcc aaa gcc aac ggc aac tag                  1575
Arg Glu Arg Arg Leu Lys Ala Lys Ala Asn Gly Asn
                515                 520

<210> SEQ ID NO 3
<211> LENGTH: 524
<212> TYPE: PRT
<213> ORGANISM: Artificial sequence
<220> FEATURE:
<223> OTHER INFORMATION: Synthetic Construct

<400> SEQUENCE: 3

Met Ser Ser Thr Thr Ser Ser Ser Arg Ser Asp Leu Glu Lys Val Pro
1               5                   10                  15

Val Pro Gln Val Ile Pro Arg Asp Ser Asp Ser Asp Lys Gly Ser Leu
                20                  25                  30

Ser Pro Glu Pro Ser Thr Leu Glu Ala Gln Ser Ser Glu Lys Pro Pro
            35                  40                  45

His His Ile Phe Thr Arg Ser Arg Lys Leu Gln Met Val Cys Ile Val
        50                  55                  60

Ser Leu Ala Ala Ile Phe Ser Pro Leu Ser Ser Asn Ile Tyr Phe Pro
65                  70                  75                  80

Ala Leu Asp Asp Val Ser Lys Ser Leu Asn Ile Ser Met Ser Leu Ala
                85                  90                  95

Thr Leu Thr Ile Thr Val Tyr Met Ile Val Gln Gly Leu Ala Pro Ser
                100                 105                 110

Phe Trp Gly Ser Met Ser Asp Ala Thr Gly Arg Arg Pro Val Phe Ile
            115                 120                 125

Gly Thr Phe Ile Val Tyr Leu Val Ala Asn Ile Ala Leu Ala Glu Ser
        130                 135                 140

Lys Asn Tyr Gly Glu Leu Met Ala Phe Arg Ala Leu Gln Ala Ala Gly
145                 150                 155                 160

Ser Ala Ala Thr Ile Ser Ile Gly Ala Gly Val Ile Gly Asp Ile Thr
                165                 170                 175

Asn Ser Glu Glu Arg Gly Ser Leu Val Gly Ile Phe Gly Gly Val Arg
                180                 185                 190

Met Leu Gly Gln Gly Ile Gly Pro Val Phe Gly Gly Ile Phe Thr Gln
            195                 200                 205

Tyr Leu Gly Tyr Arg Ser Ile Phe Trp Phe Leu Thr Ile Ala Gly Gly
        210                 215                 220

Val Ser Leu Leu Ser Ile Leu Val Leu Pro Glu Thr Leu Arg Pro
225                 230                 235                 240

Ile Ala Gly Asn Gly Thr Val Lys Leu Asn Gly Ile His Lys Pro Phe
                245                 250                 255
```

Ile Tyr Thr Ile Thr Gly Gln Thr Gly Val Val Glu Gly Ala Gln Pro
                260                 265                 270

Glu Ala Lys Thr Lys Thr Ser Trp Lys Ser Val Phe Ala Pro Leu
        275                 280                 285

Thr Phe Leu Val Glu Lys Asp Val Phe Ile Thr Leu Phe Phe Gly Ser
290                 295                 300

Ile Val Tyr Thr Val Trp Ser Met Val Thr Ser Ser Thr Thr Asp Leu
305                 310                 315                 320

Phe Ser Glu Val Tyr Gly Leu Ser Ser Leu Asp Ile Gly Leu Thr Phe
                325                 330                 335

Leu Gly Asn Gly Phe Gly Cys Met Ser Gly Ser Tyr Leu Val Gly Tyr
                340                 345                 350

Leu Met Asp Tyr Asn His Arg Leu Thr Glu Arg Glu Tyr Cys Glu Lys
                355                 360                 365

His Gly Tyr Pro Ala Gly Thr Arg Val Asn Leu Lys Ser His Pro Asp
                370                 375                 380

Phe Pro Ile Glu Val Ala Arg Met Arg Asn Thr Trp Trp Val Ile Ala
385                 390                 395                 400

Ile Phe Ile Val Thr Val Ala Leu Tyr Gly Val Ser Leu Arg Thr His
                405                 410                 415

Leu Ala Val Pro Ile Ile Leu Gln Tyr Phe Ile Ala Phe Cys Ser Thr
                420                 425                 430

Gly Leu Phe Thr Ile Asn Ser Ala Leu Val Ile Asp Leu Tyr Pro Gly
                435                 440                 445

Ala Ser Ala Ser Ala Thr Ala Val Asn Asn Leu Met Arg Cys Leu Leu
                450                 455                 460

Gly Ala Gly Gly Val Ala Ile Val Gln Pro Ile Leu Asp Ala Leu Lys
465                 470                 475                 480

Pro Asp Tyr Thr Phe Leu Leu Leu Ala Gly Ile Thr Leu Val Met Thr
                485                 490                 495

Pro Leu Leu Tyr Val Glu Asp Arg Trp Gly Pro Gly Trp Arg His Ala
                500                 505                 510

Arg Glu Arg Arg Leu Lys Ala Lys Ala Asn Gly Asn
                515                 520

<210> SEQ ID NO 4
<211> LENGTH: 40
<212> TYPE: DNA
<213> ORGANISM: Artificial sequence
<220> FEATURE:
<223> OTHER INFORMATION: Primer citT1

<400> SEQUENCE: 4
gctccaccgc ggtggcggcc gccggcgtag atcatcgcct           40

<210> SEQ ID NO 5
<211> LENGTH: 40
<212> TYPE: DNA
<213> ORGANISM: Artificial sequence
<220> FEATURE:
<223> OTHER INFORMATION: Primer citT2

<400> SEQUENCE: 5
cattatacga agttatacta gtcaacttag catacagatt           40

<210> SEQ ID NO 6
<211> LENGTH: 42

```
<212> TYPE: DNA
<213> ORGANISM: Artificial sequence
<220> FEATURE:
<223> OTHER INFORMATION: Primer citT3

<400> SEQUENCE: 6
tgctatacga agttatgttt aaactcggaa gaaagaggta gc          42

<210> SEQ ID NO 7
<211> LENGTH: 42
<212> TYPE: DNA
<213> ORGANISM: Artificial sequence
<220> FEATURE:
<223> OTHER INFORMATION: Primer citT4

<400> SEQUENCE: 7
ggcgaattcg tttgtgttaa ttaaaaacag ggatactcta ca          42

<210> SEQ ID NO 8
<211> LENGTH: 20
<212> TYPE: DNA
<213> ORGANISM: Artificial sequence
<220> FEATURE:
<223> OTHER INFORMATION: Primer citT5

<400> SEQUENCE: 8
gaaccccaga agctgggagc                                   20

<210> SEQ ID NO 9
<211> LENGTH: 20
<212> TYPE: DNA
<213> ORGANISM: Artificial sequence
<220> FEATURE:
<223> OTHER INFORMATION: Primer citT6

<400> SEQUENCE: 9
ggtagacggc ctgtctttat                                   20
```